United States Patent [19]

Lamberti et al.

[11] 4,167,561

[45] Sep. 11, 1979

[54] HYPOCHLORITE DISINFECTING COMPOSITIONS AND USE THEREOF

[75] Inventors: Vincent Lamberti, Upper Saddle River; Mark D. Konort, Haworth; Beth A. DiLorenzo, Ridgewood, all of N.J.

[73] Assignee: Lever Brothers Company, New York, N.Y.

[21] Appl. No.: 583,360

[22] Filed: Jun. 9, 1975

Related U.S. Application Data

[63] Continuation-in-part of Ser. No. 429,453, Dec. 28, 1973, abandoned.

[30] Foreign Application Priority Data

Dec. 24, 1974 [CA] Canada .................................. 216933

[51] Int. Cl.$^2$ ............................................ A01N 11/00
[52] U.S. Cl. ..................................... 424/149; 252/94; 252/107; 252/557; 71/67
[58] Field of Search .................... 424/149; 252/95, 99, 252/106, 107, 557

[56] References Cited

U.S. PATENT DOCUMENTS

| | | | |
|---|---|---|---|
| 3,689,421 | 9/1972 | Briggs | 252/95 |
| 3,714,074 | 1/1973 | Inamorato | 252/99 |

OTHER PUBLICATIONS

Chemical Abstracts, vol. 78, (1973), p. 99507r.

*Primary Examiner*—V. D. Turner
*Attorney, Agent, or Firm*—James J. Farrell; Melvin H. Kurtz; Ira J. Schultz

[57] ABSTRACT

The length of time that a disinfecting alkali-metal hypochlorite solution remains active may be controlled by providing for the presence therein of an alkali-metal alpha-hydroxy-beta-sulfosuccinate at pH 2 to 12, reducing the pH to a level below about 9.5, and heating after a desired time, the sulfosuccinate having very little reactivity with the hypochlorite at room temperature, but being more reactive to destroy substantially all of the hypochlorite at elevated temperatures.

An additional advantage of the aforementioned solution lies in the ability of the alkali-metal alpha-hydroxy-beta-sulfosuccinate to serve as a detergent builder, sequestrant, and descaling agent at appropriate concentrations and pH levels.

8 Claims, No Drawings

HYPOCHLORITE DISINFECTING COMPOSITIONS AND USE THEREOF

This application is a continuation-in-part application of copending application Ser. No. 429,453, filed Dec. 28, 1973 and now abandoned.

BACKGROUND OF THE INVENTION

1. Field of the Invention

The present invention relates to a process for disinfecting inanimate objects with an alkali-metal hypochlorite solution.

Sodium, potassium, lithium, and calcium hypochlorites are well known for their disinfecting and bleaching properties. The disinfecting properties are discussed in U.S. Pat. No. 3,717,580 to Echols et al, wherein it is disclosed that sensitive materials may be disinfected by hypochlorite solutions without prolonged exposure to residual hypochlorite.

The hypochlorite solutions of the instant invention are also useful for destroying mold, removing slime and algae, on walls or in pipes, descaling, metal ion sequestering as well as bleaching textile materials.

While the use of citrates and malates as disclosed in the aforementioned Echols et al patent, destroys residual hypochlorite on treated materials, it does not permit control or prolonging of the contact time beyond that of the automatic destructive action of that particular system.

Moreover, it is a feature of the present invention that less hypochlorite need be used initially than would be required in the use of the citrate or malate self-destruction system because in the process of the present invention the self-destruction of the hypochlorite can be delayed until the hypochlorite has completed its action.

Heretofore, the only means of cleansing the treated materials of hypochlorite was either by flushing the surface of said materials with copious amounts of water or by treating with the above-mentioned citrates or malates. The disadvantage of the former method is the eventual introduction of large quantities of hypochlorite into effluent streams and thereby causing or contributing to an imbalance in the biological population of receiving sewage treatment plants especially when the treatment plants are in close proximity to the point of effluent discharge. The disadvantage of the latter method is that, as stated hereinabove, large amounts of hypochlorite are required initially to compensate for the high degree of reactivity between the hypochlorite and the citrate or malate.

2. Discussion of the Prior Art

Pertinent prior art in this area is exemplified by U.S. Pat. No. 3,717,580 to Echols. This patent relates to the provision of a disinfecting/decontaminating solution comprising citrate and hypochlorite. The novel feature of this system is its "ability" to self-destruct after a short period of germicidal activity. The advantage of such a system is that a powerful disinfectant such as sodium hypochlorite may be used on sensitive materials without undue exposure of the treated surface to the disinfectant.

SUMMARY OF THE INVENTION

It has now been found that the length of time desired for the contacting of an object by alkali metal hypochlorite can be controlled at will by providing for the presence in the hypochlorite solution of an alkali-metal alphahydroxy-beta-sulfosuccinate, which reacts with hypochlorite to only a slight extent at and near room temperature, but reacts rapidly to destroy most or all of the hypochlorite at elevated temperatures. In the practice of the instant invention, the object to be disinfected or otherwise treated is contacted with an alkali metal hypochlorite solution. After any desired interval of time, whether still in contact with the surface or not, the solution is then heated to destroy substantially all of the hypochlorite by reaction with the aforementioned sulfosuccinate compound. In this manner a process for disinfecting surfaces with an inorganic hypochlorite is provided which insures destruction of a substantial amount of the hypochlorite after disinfection is accomplished. The hypochlorite solution can be substantially destroyed in contact with the surface or the solution can be removed and destroyed in bulk before disposed.

It is an object of the present invention to formulate a substantially stable aqueous solution containing an alkali metal or alkaline earth metal hypochlorite and an alkali metal or alkaline earth metal salt of an alpha-hydroxy-beta-sulfosuccinate as hypochlorous acid/hypochlorite scavenger.

It is another object of the invention to provide a process for controlling the length of time during which an object is in contact with a hypochlorite solution, wherein the hypochlorite is subjected to the action of the above-mentioned hypochlorite scavenger.

It is a further object of the present invention to provide sanitizing bleaching compositions having metal ion sequestrant action and/or descaling properties as well as a temperature-controlled self-destructing feature for destroying the hypochlorite/hypochlorous acid species after a selected time interval.

DETAILED DESCRIPTION OF THE INVENTION

The solutions suitable in the practice of the present invention contain an alkali-metal or alkaline-earth hypochlorite and an alkali metal or alkaline earth metal alpha-hydroxy-beta-sulfosuccinate.

Within the pH range of about 2 to about 12, the aforementioned hypochlorite and sulfosuccinate in admixture have bleaching, sanitizing, detergent, sequestrant, and descaling properties on hard surfaces. A pH level of about 4 to about 8 is preferred for general use on most glass, ceramic, and plastic surfaces, a pH of about 2 to about 6 is preferred for descaling purposes, while a pH of about 6.5 to about 12 is preferred for general use on metal surfaces. The destructive action of the alpha-hydroxy-beta-sulfosuccinates on hypochlorites is dependent to a great extent on pH; the higher the pH, the less vigorous is the destructive action at elevated temperatures. A desirable pH range is about 2 to 9.5 for destruction of the hypochlorite. Preferably the pH range is about 4 to about 8, and most suitably is about 6 to about 7.5 for rapid destruction of the hypochlorite. It is within the scope of the invention to employ the solutions at the higher pH levels, for example at a pH range within about 9.5 to 12, at which destruction of the hypochlorite is slow, and then to destroy the hypochlorite by adding an acid to lower the pH to a level below about 9.5, followed by heating to a temperature from about 35° C. to about 100° C. Phosphoric acid is the preferred acid for lowering the pH, because of its lesser tendency to be corrosive toward metals. Stated succinctly, the solutions of the instant invention are to a degree pH and temperature dependent.

Hypochlorite solutions contain both hypochlorite and hypochlorous acid species at pH levels somewhat above and below 7, at which about 73% of the hypochlorite is in the acid form. In view of the co-presence of both the salt and acid forms, the terms "hypochlorite" and "alpha-hydroxy-beta-sulfosuccinate" without designation of the cation as used herein refer to the acid forms, the salt forms, and mixtures of these forms. The cations are selected from the group consisting of sodium, potassium, lithium, calcium and hydrogen. Preferably the cations are alkali metals and hydrogen.

The concentration of hypochlorite in a disinfecting solution (i.e. a disinfecting amount) ranges from about 0.0005 molar (0.0037% by weight) to about 0.067 molar (0.5% by weight). The concentration of sulfosuccinate ranges from about 0.0005 molar to about 2 molar, e.g. in the case of the trisodium salt from about 0.014% to 56%. The molar ratio of hypochlorite to sulfosuccinate may vary from about 0.01 to 1 to about 2 to 1.

The desired pH is maintained preferably by a buffer system. A suitable buffer solution for maintaining a pH of 7 may contain, per liter, 6.81 gm of $KH_2PO_4$ and 29.65 ml of 1N NaOH.

A convenient buffer system may be derived from the sulfosuccinate itself, the mixed acid and salt forms of which may be prepared as described in Example 2 to provide a pH within the range of about 4 to about 5.5. Levels of pH from about 8.5 to about 9.5 may be provided by a mixture of 10.20 to 34.50 ml of 0.2 M NaOH, and 50 ml of a mixture of 0.2 M $H_3BO_3$ and 0.2 M KCl, diluted to 200 ml. Levels of pH from about 9.5 to about 12 may be obtained through the use of sodium metasilicate, trisodium orthophosphate, or an alkali-metal hydroxide.

The alkaline forms of the solutions containing hypochlorite and sulfosuccinate are stable against decomposition over long periods of time at room temperature. Accordingly, it is convenient to prepare stock solutions at pH levels of about 9.5 to about 12 and to lower the pH to the desired level immediately before use. Any acid of sufficient ionic strength is suitable for lowering the pH, but it is preferred to use a mineral acid such as dilute phosphoric, dilute hydrochloric or dilute sulfuric acid for economical reasons. It is preferred however, to employ separate solutions of hypochlorite and sulfosuccinate, and adjust the pH to about 6 to 7.5 immediately before use or when the self-destructing property is required.

If desired, the solution may contain a detergent surfactant or wetting agent to assist in the cleaning operation and to lower the surface tension to insure spreading of the solution for the complete coverage of metal surfaces. Any detergent species compatible with hypochlorite is suitable. Normally, these will be the anionics, quaternaries, and certain nonionics.

Examples of anionic soap detergents which can be used in admixture, if desired, are the sodium, potassium ammonium and in the compositions of the present invention alkylolammonium salts of higher detergent range fatty acids ($C_{10}$–$C_{20}$). Particularly useful are the sodium and potassium salts of the mixtures of fatty acids derived from coconut oil and tallow, i.e., sodium or potassium tallow and coconut soap. Examples of suitable anionic organic non-soap detergents in the form of their water soluble salts are: alkylglycerylethersulfonates; alkyl sulfates; alkyl monoglyceride sulfates or sulfonates; alkylpolyoxyethylene sulfates; acylsarcosinates; acyl esters of isethionates; N-acyl-N-methyl taurates, alkylbenzenesulfonates wherein the alkyl substituent is straight chain or branched chain; sulfonated alpha-olefins; alkylphenol polyoxyethylene sulfates. In these compounds the alkyl and acyl groups, respectively, contain 10 to 20 carbon atoms. They are used in the form of water soluble salts, the sodium, potassium, ammonium, and alkylolammonium salts, for example. Specific examples are: sodium lauryl sulfate, sodium tallow alkyl sulfate; sodium salt of sulfonated alpha-tridecene; potassium N-methyl-N-lauroyl taurate; triethanolammonium tetrapropylbenzene sulfonate; sodium (linear) dodecyl benzene sulfonate.

Examples of nonionic organic detergents which can be used in the compositions of this invention, if desired are: polyethylene oxide condensates of alkylphenols wherein the alkyl group contains from 8 to 15 carbon atoms (e.g., 1-octylphenol) and the ethylene oxide is present in a molar ratio of ethylene oxide to alkylphenol in the range of 3:1 to 20:1; condensation products of ethylene oxide with the product resulting from the reaction of propylene oxide and ethylene diamine wherein the molecular weight of the condensation products ranges from 5000 to 11,000; the condensation products of from about 5 to 30 moles of ethylene oxide with one mole of a straight or branched chain aliphatic alcohol containing from 8 to 18 carbon atoms, e.g., condensation products of 6 moles of ethylene oxide with one mole of lauryl alcohol; higher alkyl di-lower alkyl amine or phosphine oxides, e.g., dodecyldimethylamine oxide or dodecyldimethyl phosphone oxide; alkyl methyl sulfoxides such as dodecyl methyl sulfoxide.

Zwitterionic synthetic detergents can be broadly described as derivatives of aliphatic quaternary ammonium, phosphonium, and ternary sulfonium compounds, in which the aliphatic radical may be straight chain or branched, and wherein one of the aliphatic substituents contains from 10 to 18 carbon atoms and one contains an anionic water solubilization group, e.g., carboxy, sulfo, or sulfato. Examples of compounds falling within this definition are: 3-(N,N-dimethyl-N-hexadecylammonio)-2-hydroxypropane-1-sulfonate and the corresponding dodecyl and tetradecyl homologs and 3-(N,N-dimethyl-N-dodecylammonio)-propane-1-sulfonate and the corresponding hexadecyl and tetradecyl homologs.

Among the articles which can be disinfected by the process of the present invention are surgical instruments, walls, dairy equipment, equipment for processing other edible substances, reactor tanks, inaccessible parts of equipment, etc. The invention finds its greatest utility in the disinfecting of large manufacturing equipment requiring large amounts of hypochlorite. By destroying all or most of the residual hypochlorite after the disinfecting action, only a small amount, at most, of hypochlorite is directed into the effluent stream, thus minimizing destruction of desired bacteria in effluent waters receiving treatment plants.

In accordance with the process of the instant invention, an article to be disinfected, for example in the case of a jacketed reactor, the system is filled with an aqueous solution of an alkali-metal hypochlorite and an alkali-metal alpha-hydroxy-beta-sulfosuccinate at concentrations set forth hereinabove. After the passage of a desired length of time of contact, the pH is adjusted, if necessary, to about 6 to about 7.5, and the solution is heated, for example in this instance by passing steam through the jacket, from about 50° C. to about 100° C. for about 5 minutes to about 2 hours and until at least about 75% of the residual hypochlorite is destroyed. The reactor is then rinsed with hot water.

The invention is more fully described in the following Examples, which are illustrative, but are not to be considered limitative, of the invention.

EXAMPLE 1

Preparation of Trisodium Alpha-Hydroxy-Beta-Sulfosuccinate

Sulfomaleic anhydride is prepared by heating a stirred mixed of 173 g of liquid sulfur trioxide and 212 g of powdered maleic anhydride to about 57° C. at which point an exothermic reaction sets in. The temperature is maintained first at 60°–66° C. with cooling and then at 50° C. overnight. The batch is finally finished by heating at 110° C. for 3 hours. NMR analysis of the product shows a conversion of 82% (mole %) of the maleic anhydride into sulfomaleic anhydride. Higher conversions are obtained by utilizing a higher ratio of sulfur trioxide to maleic anhydride.

The crude sulfomaleic anhydride prepared above is then added gradually to 150 g of crushed ice while cooling the vessel with an external cooling bath. The resulting solution is then extracted twenty-five times with 50–100 ml of ethyl ether to remove unsulfonated materials. The aqueous layer which contains purified sulfomaleic acid is then heated at 80° C. for 6½ hours to convert the sulfomaleic acid into alpha-hydroxy-beta-sulfosuccinic acid. The solution is then cooled to 60° C. and decolorized with three successive charcoal treatments. The final filtrate is then concentrated to ~250 cc., neutralized to pH=8.6 with sodium hydroxide solution and finally evaporated to dryness in vacuo followed by drying over $P_2O_5$ in a dessicator. The yield of white crystalline trisodium alpha-hydroxy-beta-sulfosuccinate is over 200 g and contains 85% active by NMR analysis (internal standard of K biphthalate; $D_2O$) and 12.6% water by standard xylol moisture analysis.

Alternatively, a technical grade product which is quite adequate for commercial use is obtained by simply adding (gradually) the crude sulfomaleic anhydride to water and heating at 80° C. for about 6 hours. The resulting solution is then neutralized to the desired pH (depending on the use intended as shown, for instance, in the following Examples) with a suitable base and either stored as a solution (e.g. especially if on the acid side) or evaporated to a solid product.

EXAMPLE 2

Preparation of Mixed Acid and Salt Forms of the Product of Example 1

A quantity of the product as prepared in Example 1 is partially neutralized to a desired pH level, preferably 4–5.5 and evaporated to dryness. The residue contains mixed acid and salt forms, the proportions of each being predeterminable by pH titrations of known acid species.

EXAMPLE 3

This example shows the increase in the destruction of sodium hypochlorite with time by trisodium alpha-hydroxy-beta-sulfosuccinate, at pH 7 and at two temperature levels, i.e., 25° C. and 50° C.

A solution of sodium hypochlorite is prepared by diluting 20 ml of a commercial household bleach, having a specific gravity of 1.08 and containing 5.06% NaOCl, to 500 ml with a pH 7 buffer solution containing 6.81 grams of $KH_2PO_4$ and 29.65 ml of 1 N NaOH per liter of solution. A 100 ml aliquot of this solution is diluted to 500 ml with the aforementioned buffer solution, and a small known quantity removed to determine the initial hypochlorite concentration. Next is added trisodium alpha-hydroxy-beta-sulfosuccinate in particulate form and dissolved to a concentration of 1.35 millimoles per 500 milliliters. One half of the solution is held at 25° C. and the other held at 50° C. Aliquots are removed periodically and the amount of remaining hypochlorite determined. Blanks without the sulfosuccinate are carried along concurrently.

The solutions contain in admixture NaOCl and sulfosuccinate in the molar ratio of about 2.2 to 1. The NaOCl is present at a concentration approximately 400 ppm.

Table I below illustrates the extent of destruction of hypochlorite with time under the conditions set forth above. The figures are corrected for the blanks, i.e., decomposition due to temperature and time alone.

TABLE I

| Time, Minutes | Percent Hypochlorite Consumed | |
|---|---|---|
| | 25° C. | 50° C. |
| 5 | 3.8 | 8.5 |
| 10 | 5.2 | 13.3 |
| 20 | 6.5 | 20.3 |
| 30 | 7.9 | 26.5 |
| 40 | 10.1 | 30.6 |
| 60 | 12.8 | 40.3 |

EXAMPLE 4

Following the procedure of Example 3, the table below shows the effect of the sulfosuccinate on the hypochlorite at a pH of 7 and a temperature of 73° C. The solution contains NaOCl and sulfosuccinate in the molar ratio of 1.95 to 1.

TABLE II

| Time, Minutes | Percent Hypochlorite Consumed |
|---|---|
| | 73° C. |
| 5 | 23.5 |
| 10 | 33.3 |
| 20 | 49.3 |
| 30 | 64.7 |
| 40 | 83.6 |
| 60 | 94.5 |

EXAMPLE 5

The following table illustrates the effect of the sulfosuccinate on the hypochlorite at a pH of 9.3 and at 50° C. and 74° C.

TABLE III

| Time, Minutes | Percent Hypochlorite Consumed | |
|---|---|---|
| | 50° C.[a] | 74° C.[b] |
| 5 | 0.83 | 2.9 |
| 10 | 0.83 | 4.5 |
| 20 | 1.33 | 6.5 |
| 30 | 1.16 | 6.9 |
| 40 | 1.16 | 9.4 |
| 60 | 2.49 | 10.8 |

[a] the solution contains NaOCl and sulfosuccinate in the molar ratio of 2.27 to 1.
[b] the solution contains NaOCl and sulfosuccinate in the molar ratio of 1.90 to 1.

The above illustrates the stability of the system under moderately alkaline conditions. In order to destroy the hypochlorite after the cleaning and sanitization has been completed, all that is required is the addition of acid to lower the pH to about 7.

EXAMPLE 6

The table below illustrates the effect of sulfosuccinate on the hypochlorite at 74° C. at a pH of 7.0 and 9.3 where the molar ratio of the hypochlorite to sulfosuccinate is 1:4.

TABLE IV

| Time, Minutes | pH 7 | pH 9.3 |
| --- | --- | --- |
| 5 | 88.8 | 16.2 |
| 10 | 96.8 | 25.6 |
| 20 | 99.0 | 34.5 |
| 30 | — | 43.2 |
| 40 | — | 52.1 |
| 60 | — | 62.5 |

The above data illustrate that the rate of destruction of the hypochlorite in the compositions of the present invention is controlled by pH, temperature, and the ratio of alkali-metal alpha-hydroxy-beta-sulfosuccinate to inorganic hypochlorite.

Although only the trisodium salt of the alpha-hydroxy-beta-sulfosuccinate is illustrated, similar results are obtained when the cations are potassium, lithium, calcium or hydrogen.

EXAMPLE 7

The walls of a food-processing plant are washed at room temperature with the following solution:

|  | Percent By Weight |
| --- | --- |
| Pluronic L62[a] | 0.20 |
| Sodium hypochlorite | 0.20 |
| Sodium alpha-hydroxy-beta-sulfosuccinate | 0.40 |
| Buffer[b] | 0.73 |
| Water | 97.47 |
|  | 100.00 |

[a] a nonionic surfactant sold by Wyandotte Chemical Corp., and which is an ethylene oxide condensate of a polyoxypropylene glycol containing about 20% ethylene oxide by weight.
[b] a mixture of $KH_2PO_4$ and $KNaHPO_4$ to provide a pH of 7.

Fifteen minutes after washing, steam at 100° C. is impringed on all areas of the walls, and the water of condensation is allowed to run off into the sewer drain.

Having described the invention, modifications within the spirit thereof will occur to those skilled in the art, and the invention is to be limited only within the scope of the appended claims.

What is claimed is:
1. A process for disinfecting a surface with an inorganic hypochlorite solution which process insures destruction of a substantial amount of said hypochlorite after said disinfection comprising:
 (i) contacting said surface with an aqueous solution consisting essentially of a disinfecting amount of said inorganic hypochlorite having a cation associated therewith, said cation being selected from the group consisting of alkali metal, alkaline earth metal, hydrogen and mixtures thereof and an alkali metal or alkaline earth metal alpha-hydroxy-beta-sulfosuccinate, the molar ratio of said hypochlorite to said alpha-hydroxy-beta-sulfosuccinate being about 0.01 to 1 to about 2 to 1 and said solution having a pH of about 2 to about 9.5, and
 (ii) heating said solution until at least about 75% of said inorganic hypochlorite is destroyed.
2. A process as defined in claim 1 wherein said solution contains about 0.0037% to about 0.5% by weight of hypochlorite and about 0.014% to about 56% of the trisodium salt of alpha-hydroxy-beta-sulfosuccinate.
3. A process as defined in claim 1 wherein the pH of said solution is lowered from about 9.5 to a range of about 6.0 to about 7.5 immediately before use.
4. A process as defined in claim 1 wherein said cation associated with said hypochlorite is selected from the group consisting of sodium, potassium, lithium and calcium.
5. A process as defined in claim 1 wherein said alpha-hydroxy-beta-sulfosuccinate is selected from the group consisting of monosodium, disodium, trisodium, monopotassium, dipostassium, and tripotassium-alpha-hydroxy-beta-sulfosuccinate, and mixtures thereof.
6. A process as defined in claim 1 further comprising heating said solution in contact with said surface.
7. An aqueous disinfectant solution consisting essentially of about 0.0037% to about 0.5% hypochlorite, and about 0.014% to about 56% of an alkali metal alpha-hydroxy-beta-sulfosuccinate and water, the molar ratio of said hypochlorite to said alpha-hydroxy-beta-sulfosuccinate being about 0.01 to 1 to about 2 to 1, said hypochlorite having a cation associated therewith wherein the cation is selected from the group consisting of sodium, potassium, lithium, hydrogen, and mixtures thereof.
8. An aqueous disinfectant solution as defined in claim 7 having a pH of about 9.5 to about 12.

* * * * *

UNITED STATES PATENT AND TRADEMARK OFFICE
CERTIFICATE OF CORRECTION

PATENT NO. : 4,167,561
DATED : September 11, 1979
INVENTOR(S) : Vincent Lamberti et al It is certified that error appears in the above-identified patent and that said Letters Patent are hereby corrected as shown below:

Col. 2, line 1: Change "alphahydroxy-beta-sulfosuccinate" to --alpha-hydroxy-beta-sulfosuccinate--.

Col. 4, line 30: Change "phosphone" to --phosphine--.

Column 5, line 11: Change "stirred mixed of" to --stirred mixture of--.

Column 7, line 41: Change "Water 97.47" to --Water 98.47--.

Column 7, Table IV: The heading "Percent Hypochlorite Consumed" should be added (See Tables 1, 2 and 3)

Column 7, line 48: Change "impringed" to --impinged--.

Signed and Sealed this

Fourth Day of December 1979

[SEAL]

Attest:

SIDNEY A. DIAMOND

Attesting Officer

Commissioner of Patents and Trademarks